United States Patent [19]
Stanley, Jr.

[11] Patent Number: 5,413,768
[45] Date of Patent: * May 9, 1995

[54] FLUID DECONTAMINATION APPARATUS HAVING PROTECTED WINDOW

[76] Inventor: E. Glynn Stanley, Jr., 372 Blue Jay Way, Napa, Calif. 94559

[*] Notice: The portion of the term of this patent subsequent to Jun. 9, 2009 has been disclaimed.

[21] Appl. No.: 73,827

[22] Filed: Jun. 8, 1993

[51] Int. Cl.⁶ .............................................. B01J 19/08
[52] U.S. Cl. .................................. 422/186.3; 422/168; 422/24; 210/95; 210/198.1; 210/748; 210/759; 210/760; 210/205; 250/435
[58] Field of Search ................ 210/94, 95, 198.1, 205, 210/748, 759, 760; 422/24, 186.3, 186.07, 168; 250/432, 435, 436, 437; 219/121.8, 121.84

[56] References Cited

U.S. PATENT DOCUMENTS

| | | | |
|---|---|---|---|
| 3,634,025 | 1/1972 | Landry | 21/102 |
| 3,700,406 | 10/1972 | Landry | 250/437 |
| 3,894,236 | 7/1975 | Hazelrigg | 250/435 |
| 4,101,777 | 7/1978 | Reid | 250/436 |
| 4,179,616 | 12/1979 | Coviello et al. | 250/527 |
| 4,230,571 | 10/1980 | Dadd | 210/760 |
| 4,265,747 | 5/1981 | Copa et al. | 210/758 |
| 4,273,660 | 6/1981 | Beitzel | 210/760 |
| 4,274,970 | 6/1981 | Beitzel | 210/748 |
| 4,327,276 | 4/1982 | Injushin et al. | 219/121 |
| 4,548,716 | 10/1985 | Boeve | 210/652 |
| 4,609,471 | 9/1986 | Beemster et al. | 210/748 |
| 4,661,264 | 4/1987 | Goudy, Jr. | 210/748 |
| 4,752,401 | 6/1988 | Bodenstein | 210/746 |
| 4,792,407 | 12/1988 | Zeff et al. | 210/748 |
| 4,798,702 | 1/1989 | Tucker | 422/24 |
| 4,816,145 | 3/1989 | Goudy, Jr. | 210/96.1 |
| 4,913,827 | 4/1990 | Nebel | 210/748 |
| 5,120,450 | 6/1992 | Stanley, Jr. | 210/748 |

FOREIGN PATENT DOCUMENTS 2048-092-A 8/1988 Japan .

OTHER PUBLICATIONS

H. Baumann et al., "On Line Organic Removal In Ultrapure Water Systems With An Electrochemical Ozonizer," Seventh Annual Semiconductor Pure Water Conference, Jan. 14–15, 1988, Santa Clara Convention Center, Santa Clara, Calif., pp. 307–321.

Robert W. Legan, "Ultraviolet Light Takes On CPI Role," Chemical Engineering, Jan. 25, 1982, pp,. 95–100.

William W. Nebel et al., "Purification of Deionized Water by Oxidation With Ozone," Solid State Technology, Oct. 1984, pp. 185–193.

"Light Sources Germicidal Lamps," Technical Bulletin #1, 5 pages.

"Ultraviolet Disinfection Systems," Ultraviolet Technology, 3 pages.

D. W. Camp, "Effect of Lamp-Coating Mineral Deposits on UV-Oxidation of Ground Water", Lawrence Livermore National Laboratory, Nov. 1991, pp. 1–11.

Primary Examiner—Robert A. Dawson
Assistant Examiner—Robert James Popovics
Attorney, Agent, or Firm—Skjerven, Morrill, MacPherson, Franklin & Friel; Brian D. Ogonowsky

[57] ABSTRACT

An ultraviolet radiation exposure fluid decontamination apparatus is provided which includes a container made of high tensile strength material through which the fluid to be treated flows, a high intensity, directed beam light source, and an ultraviolet transparent window through which the directed beam propagates. The container interior has a reflective surface which distributes the light throughout the container. A non-stick material lines the container interior which prevents fouling of the container. The window is also protected by a similar non-stick material. Organic contaminates are oxidized to carbon dioxide, water and other nonharmful products during the fluid treatment carried out by this apparatus.

13 Claims, 4 Drawing Sheets

FLUID DECONTAMINATION APPARATUS HAVING PROTECTED WINDOW

FIELD OF THE INVENTION

This invention relates to an ultraviolet radiation exposure apparatus for the decontamination of fluids using a high intensity, directed light source and a fluid container having a protected window.

BACKGROUND OF THE INVENTION

The combination of ultraviolet radiation and oxidant, or the use of ultraviolet radiation alone, is a powerful tool for the removal of organic and microbial contaminants from fluids, particularly water. Both hydrogen peroxide and ozone are suitable oxidants for use in ultraviolet radiation/oxidation systems, but ozone is more economical and therefore more often used.

Ozone alone is a strong oxidizing agent that can react with all oxidizable contaminants in the fluid; however, the rate of oxidation can be enhanced by the simultaneous application of ultraviolet radiation. According to equation 1, ultraviolet radiation accelerates the decay of ozone dissolved in water to the hydroxyl radical (.OH), one of the most powerful oxidants known.

$$O_3 + H_2O \xrightarrow{UV} 2\ OH + O_2 \xrightarrow{organics} \text{Oxidation Products} \quad (1)$$

Oxidation of organic contaminants by ultraviolet radiation and ozone ultimately yields non-harmful products consisting of carbon dioxide, water and oxygen according to equation 2. The application of ultraviolet radiation and ozone for control of microbial contamination is also a very efficient process because the cell wall of the microorganism is ruptured, killing the organism.

$$C_xH_yO_2 + O_3 \xrightarrow{UV} CO_2 + H_2O + O_2 \quad (2)$$

Known ultraviolet radiation/oxidation systems suffer a serious disadvantage, however. Typically, a germicidal ultraviolet lamp is enclosed in a sleeve which is immersed in the fluid to be treated so that the ultraviolet radiation propagates through the fluid. In prior art systems, these sleeves have been made of quartz, one of the few materials that is transparent to the high energy, short wavelength ultraviolet light that promotes the reactions described above.

Quartz sleeves often require cleaning due to water caused fouling. A film tends to accumulate on the quartz sleeve which decreases transmission of the ultraviolet radiation to the fluid. The frequent mechanical or chemical cleaning which is required to remove the film is extremely inefficient since it requires shutting down the fluid decontamination system and draining the fluid to reach the surfaces needing cleaning. Furthermore, quartz which is subjected to ultraviolet light is solarized, producing a slightly tan color in the quartz, which also reduces transmission. Most importantly, quartz sleeves are fragile and expensive.

Immersion of the quartz sleeve in the fluid to be treated disrupts the straight forward flow of the fluid through the reaction vessel and creates eddies and subcurrents such that all the fluid is not irradiated or exposed to the oxidant to an equal extent. Therefore, the contaminants are inefficiently treated.

SUMMARY OF THE INVENTION

According to this invention, an ultraviolet radiation exposure apparatus is provided which minimizes the disadvantages associated with quartz and immersion of a quartz sleeve into the fluid to be treated. In addition, the ultraviolet radiation exposure apparatus of this invention allows fluid treatment at high or low pressures and it tolerates sudden pressure changes.

One embodiment of this invention provides a high tensile strength alloy or steel container with a reflective interior surface that is lined with an inert, non-sticking material which is transparent to ultraviolet radiation, such as fluorinated ethylene propylene (FEP). The non-stick nature of FEP prevents fouling of the container's interior which simplifies cleaning and maintenance of the ultraviolet radiation exposure apparatus. Optionally, an oxidant is injected into the fluid which is irradiated with ultraviolet light while in the container.

A high intensity, directed beam of ultraviolet radiation enters the container through an ultraviolet-transparent window, and because the beam is directed, the window can be relatively small. The window is preferably quartz. The quartz window is lined with, or otherwise protected by, a layer of FEP to prevent fouling of the window, further simplifying maintenance of the apparatus. The FEP protective layer is held in place within the container by any suitable surface feature formed inside the container.

The use of a directed, high intensity light source rather than a diffuse light source, such as the germicidal lamps used in the prior art, eliminates the need for reflectors or some other system of collecting and directing the diffuse light. The use of high intensity light according to this invention directs more lumens per unit time through the fluid, and thus promotes the desired oxidation more efficiently, leading to shorter reaction times.

The reflective interior surface of the container repeatedly reflects the ultraviolet radiation, thereby irradiating a substantial portion of the container's volume. The ultraviolet transparent lining which covers the reflective interior surface allows this reflection.

The high tensile strength material forming the container allows the treatment of fluids at high or low pressures and tolerates sudden pressure changes.

By avoiding immersion of an ultraviolet lamp and its quartz sleeve into the fluid, the apparatus according to this invention allows straightforward flow of the fluid, and therefore avoids the generation of eddies and subcurrents that can cause some portions of the fluid to be inefficiently treated.

DETAILED DESCRIPTION OF THE INVENTION

Figure 1:
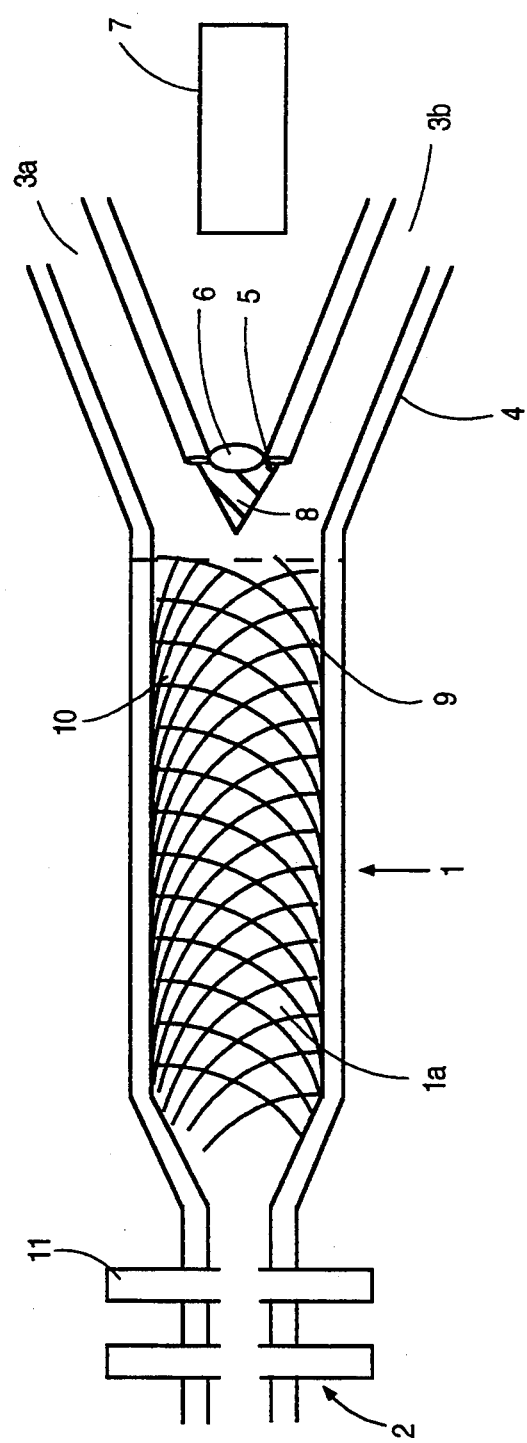
FIG. 1 is a sectional view of one embodiment of an ultraviolet radiation exposure apparatus according to this invention.

Referring to FIG. 1, fluid enters a high tensile strength alloy or steel container 1 from inflow source 2. Fluid exits the container 1 through an out-flow chamber 3 having one or more dispersing pipes, shown here as pipes 3a and 3b, also made of a high tensile strength material. Out-flow chamber 3 and container 1, which may form a Y-shape, are joined as described below. At the base of the converging pipes 3a and 3b, a window 6 is seated in an opening which is sealed like a port-hole with an ozone impervious gasket 5 and any suitable plates (not shown). The light source 7 produces a high intensity ultraviolet light beam directed toward window 6, where window 6 is made of a material transparent to ultraviolet radiation, such as quartz.

The interior of container 1 is formed with a surface 9 that is highly reflective to ultraviolet radiation, such as polished aluminum. The light beam from light source 7 passes through window 6 and is repeatedly reflected by the interior of container 1 so that a substantial portion of the volume of container 1 is irradiated. Window 6 can be formed so that the light beam from light source 7 is flared by passing through window 6, thereby irradiating a substantial portion of the container's volume. The light may also be scattered throughout container 1 by ridges (shown in FIG. 5) formed by routing the interior of container 1. Reflective inner surface 9 covers the entire interior of container 1, both the ridged and routed areas.

The interiors of container 1 and out-flow chamber 3 are lined with a lining 10 and 4, respectively, where the lining 4, 10 material is substantially chemically inert under conditions encountered by the apparatus during oxidation of organic contaminants. The lining 10 should also be transparent to ultraviolet radiation so that the lining 10 does not prevent reflection of ultraviolet radiation by surface 9. The lining 10 will protect container 1 and inflow source 2, and lining 4 will protect out-flow chamber 3, from corrosion and fouling caused by the contaminants in the fluids to be treated. Window 6 is similarly protected by protective lining 8, which can be integrally formed with lining 4 or 10, or formed as a separate piece. The cone shape of lining 8 will facilitate fluid flow and aid in the prevention of eddies and subcurrents by directing the fluid flow to pipes 3a and 3b; however, the preferred shape of lining 8 in an actual embodiment will depend on the particular shape of the apparatus and other factors. The linings 10, 4 and 8 may be attached to the reaction vessel by any suitable, fluid-tight means as described below.

Fluoridated ethylene propylene (FEP) can provide the non wetting, non-sticking, but ultraviolet transparent linings 10, 4 and 8 required. This chemically inert material prevents film accumulation on the interior walls of container 1, on window 6, and on the walls of out-flow chamber 3 caused by contaminants in the fluid being treated, thereby simplifying cleaning and maintenance of the apparatus. Prevention or removal of film accumulated on the interior of container 1 and window 6 is important because the film would decrease the reflectivity of reflective surface 9 and decrease the transparency of window 6, and therefore would decrease the efficiency of ultraviolet light transfer throughout container 1. FEP will not deteriorate under long exposure to ultraviolet light.

The base of inflow source 2 has an optional injection port 11 for injecting an oxidant such as hydrogen peroxide or ozone. Ozone can be produced as needed with an ozone generator according to well known methods. A plurality of injection ports may be used to increase the quantity and the rate of oxidant addition.

Figure 2:
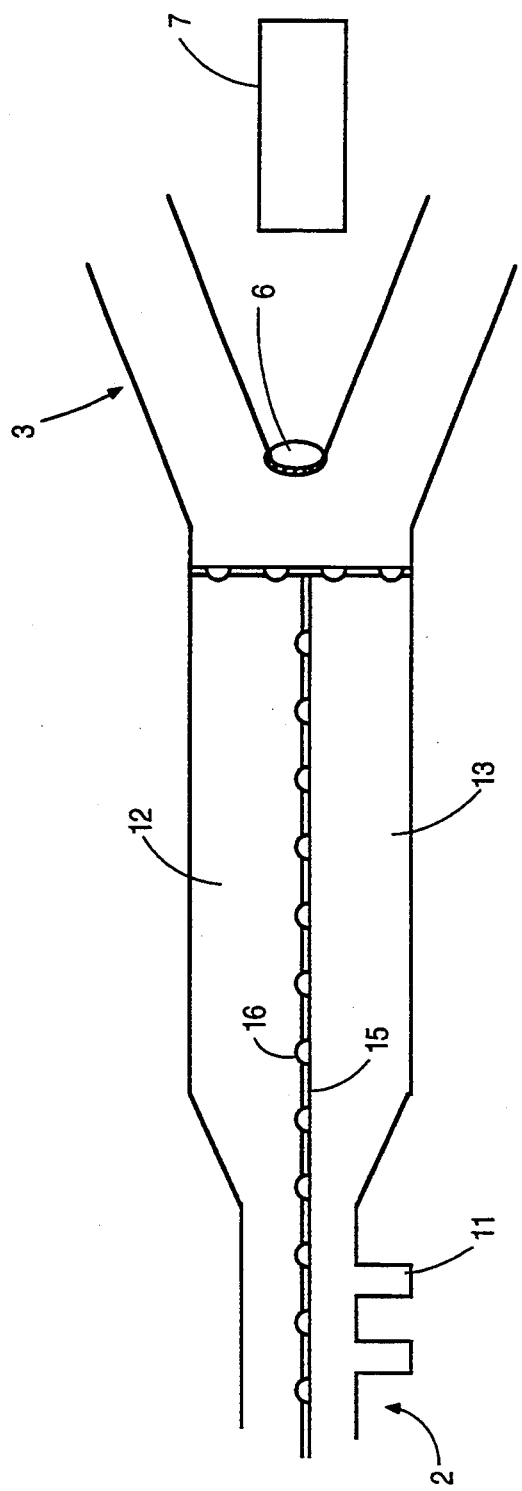
FIG. 2 is a side view of the assembled apparatus shown in FIG. 1.
Figure 3:
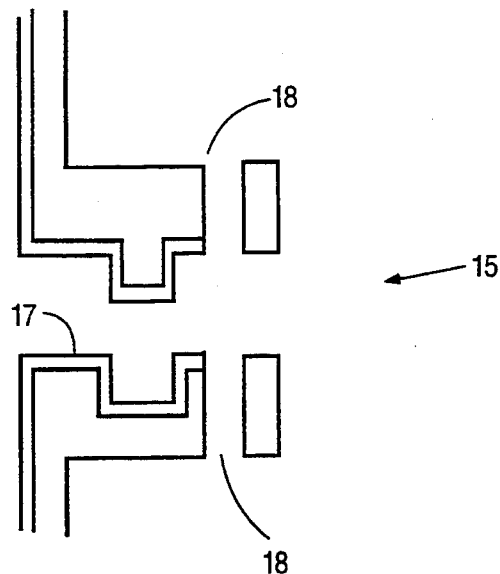
FIG. 3 shows a typical mated flange for joining the sections of the apparatus in FIG. 2.

FIG. 2 illustrates a side view of the apparatus described above. Container 1 and inflow source 2 are assembled from two half shells, upper half 12 and lower half 13, both of which have flanged edges 15 which are mated and securely fastened with bolts 16. Out-flow chamber 3 is a solid, one piece unit also having a flange 15 which mates with a flange of assembled container 1 and is fastened to container 1 with bolts 16. A typical mated flange 15 is shown in FIG. 3. Gasket 17 is made of a material which is impervious to ozone, such as teflon, and is positioned to form a fluid-tight seal between the joined, bolted sections. The bolt 16 is inserted through bolt hole 18.

Because the apparatus can be disassembled and the interior is easily accessible, this construction simplifies cleaning and maintenance of the interior, including replacement of the linings 10, 4, and 8 and of the window 6. The lining 10 can be formed in 2 pieces which fit halves 12 and 13 so that each half will be lined by one continuous segment of fluorinated ethylene propylene material. The lining 4 may, in one embodiment, be integrally formed with cone shaped lining 8, and the resulting lining can be formed as a one piece unit which conforms to the one-piece out-flow chamber 3. The linings 10 and 4 may extend to a position between mated flanges 15 so that the linings act as a gasket. This configuration also insures secure attachment of the linings 10 and 4 to the container 1 and the out-flow chamber 3, respectively.

Figure 5:
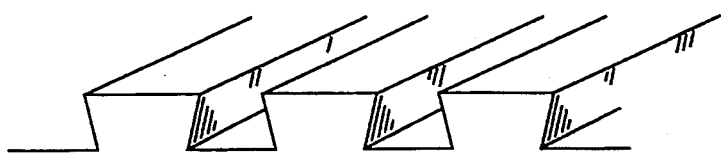
FIG. 5 is a magnified view of the non-linear inner surface of the container for securing the fluorinated ethylene propylene (FEP) coating in place.

Ridges formed by routing the interior of container 1 will also stabilize placement of the lining 10 in container 1. FIG. 5 shows a magnified view of the ridges formed in container 1. The ridges are preferably arranged in a criss-cross, diamond pattern. Lining 10 is pressed or molded to fill the routed areas and covers the ridges so that the interior of container 1 presents a smooth, lined surface. Consequently, lining 10 is formed with a varying thickness having indentations corresponding to the ridges of container 1. The coupling of these ridges and indentations prohibits any movement of lining 10 relative to container 1 by locking the lining 10 in place. The smooth surface of lining 10 facilitates direct fluid flow, as is necessary to prevent the generation of eddies and subcurrents in the reaction vessel.

Figure 4:
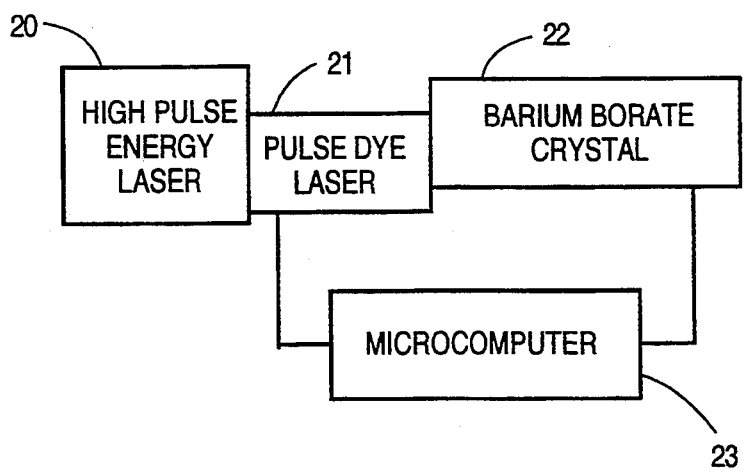
FIG. 4 is a schematic view of a laser system for producing a directed beam of ultraviolet light.

The light source 7 may be a laser or a configuration of lasers according to FIG. 4. High pulse energy Nd:YAG laser 20 produces a beam with a wavelength of 355 nm which acts as a pump source for the pulsed dye laser 21. The dye for pulsed dye laser 21 is chosen to allow the laser configuration according to FIG. 4 to ultimately produce an output beam in the ultraviolet range. The frequency of the beam from pulsed dye laser 21 is doubled using a barium-borate crystal 22 to achieve the desired wavelength spectrum. A microprocessor scan control unit 23 is connected to both the pulsed dye laser 21 and the barium-borate crystal 22 to control the final wavelength of light produced.

With this configuration of lasers, a beam with a wavelength of 254 nm can be produced and directed through window 6 into container 1. This wavelength, which is diffusely produced by germicidal lamps, is known to be effective for promoting the oxidation of organic contaminates in the presence of an oxidant.

In another embodiment, light source 7 may be an electron-beam-pumped excimer laser or other suitable laser which outputs UV radiation at, for example, 193 nm. In one embodiment, the laser outputs 150 watts, or more, continuous power and provides 10 nm pulses of radiation energy.

Figure 6:
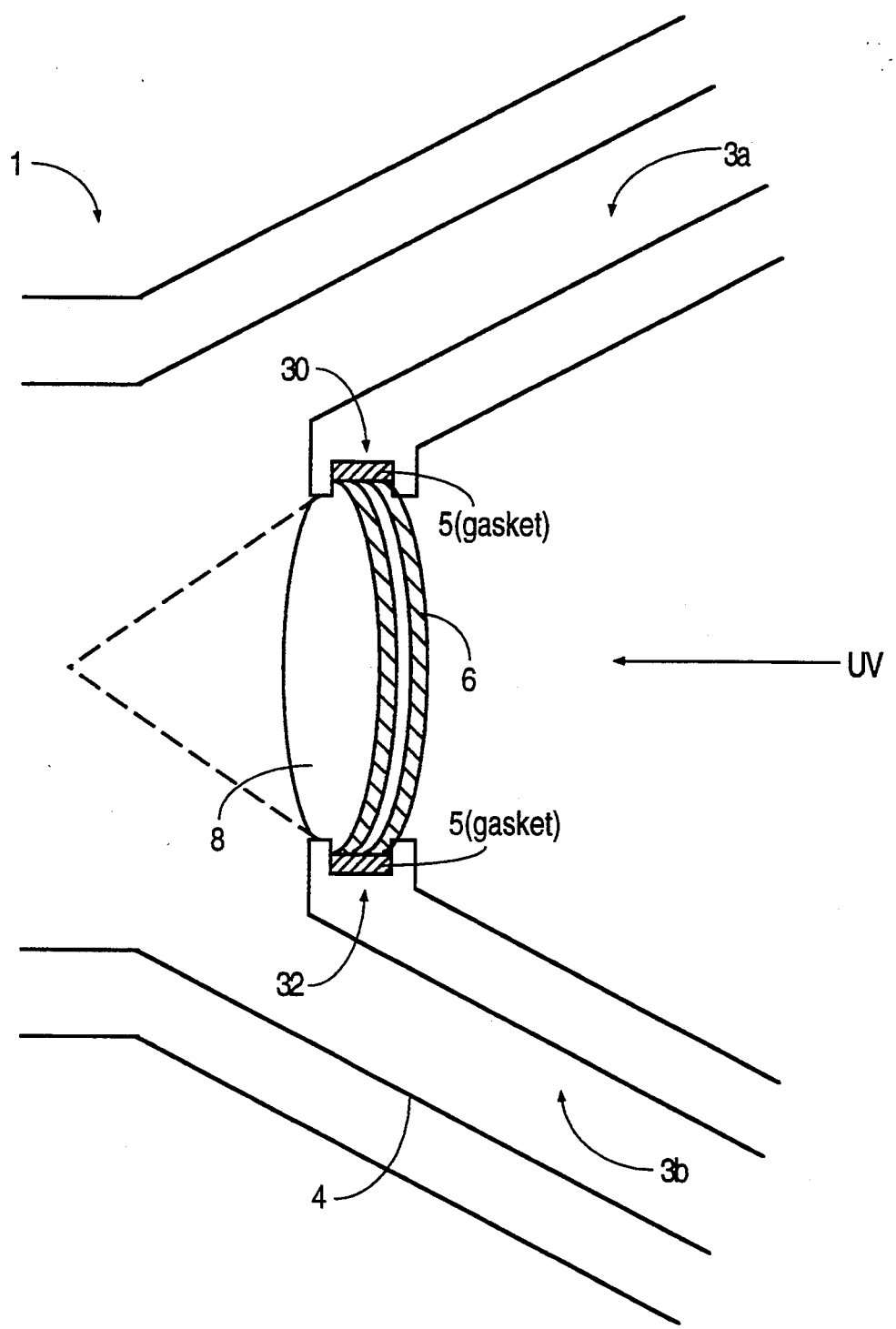
FIG. 6 is a magnified view of the window area in the apparatus of FIG. 1 showing the FEP protective layer being held in place by the same ridges holding the window in place.

FIG. 6 is a more detailed illustration of window 6 and lining 8 secured within container 1. Window 6 is held in place with respect to container 1 by ridges 30 and 32 formed in container 1. Gasket 5 forms a tight seal between container 1 and window 6. Since lining 8 is formed of a substantially non-stick material, such as FEP, lining 8 will not adhere directly to the smooth quartz window 6. Therefore, lining 8, formed as a separate lining piece, is formed in FIG. 6 so as to use ridges 30 and 32 as anchors to container 1. Alternatively, any non-linear surface, such as protruberances, can be formed on the inner surface of container 1 to provide an anchor for lining 8 to be secured to.

Although in FIG. 1, lining 8 is shown as having a triangular or cone shape, FIG. 6 illustrates that lining 8 may also be a flat piece.

In the preferred embodiment, the FEP lining 8 is approximately 10 mm thick or less and is partially supported by window 6 for stabilization against the fluid and vacuum forces within container 1. Also, in the preferred embodiment, lining 8 is made easily removable and replaceable to maintain the high transparency of lining 8.

The size and shape of window 6 and lining 8 will depend upon the light source used and the container 1 size and shape. In one embodiment, window 6 may be 8×8 inches, with a corresponding size of lining 8.

The apparatus of FIG. 1 can be operated with a continuous flow of fluid. Alternatively, longer reaction times may be achieved by recirculating the fluid from the dispersing pipes 3a and 3b to the inflow source 2 or by holding the fluid in container 1 while continuing oxidant injection and ultraviolet irradiation.

The flow rate of the fluid, the rate of oxidant injection and the wavelength of the laser output beam can be adjusted to achieve optimum results, meaning minimum residual contamination in practically short reaction times. The optimum conditions will depend on the degree of initial contamination, the desired level of purification, the nature of the contaminants, and the amount of fluid to be treated.

While particular embodiments of the present invention have been shown and described, it will be obvious to those skilled in the art that changes and modifications may be made within departing from this invention in its broader aspects and, therefore, the appended claims are to encompass within their scope all such changes and modifications as fall within the true spirit and scope of this invention.

I claim:

1. A fluid decontamination apparatus comprising:

a reaction vessel through which fluid flows, said reaction vessel having a substantially planar window substantially transparent to ultraviolet radiation, said window being formed of a material different than a material used to form said reaction vessel;

an inlet connected to said reaction vessel through which fluid enters said reaction vessel;

an outlet connected to said reaction vessel through which fluid exits said reaction vessel;

an ultraviolet radiation source positioned external to said reaction vessel so that said ultraviolet radiation propagates through said window, said ultraviolet radiation being sufficient to promote the oxidation of organic contaminants in said fluid; and a protective layer formed of a material substantially transparent to said ultraviolet radiation and substantially chemically inert, said protective layer being positioned within said vessel and interposed between said window and an inner cavity of said vessel to protect said window from contaminants in said fluid, said protective layer being at least partially held in position with respect to said window by an anchoring means forming part of said reaction vessel.

2. The apparatus of claim 1 wherein said reaction vessel has a reflective interior surface.

3. The apparatus of claim 2 wherein said reaction vessel is lined with a substantially chemically inert substance, said substance being substantially transparent to ultraviolet radiation.

4. The apparatus of claim 3, wherein said substantially chemically inert substance is fluorinated ethylene propylene.

5. The apparatus of claim 1 wherein said reaction vessel has an inner surface having surface irregularities, and said protective layer covers at least a portion of said inner surface, said surface irregularities anchoring said protective layer in place within said vessel.

6. The apparatus of claim 5 wherein said surface irregularities comprise a plurality of ridges.

7. The apparatus of claim 5 wherein said surface irregularities comprise a plurality of protuberances.

8. The apparatus of claim 1 wherein said protective layer comprises fluorinated ethylene propylene.

9. The apparatus of claim 1 wherein said protective layer is secured in place within said vessel by surface irregularities formed on an interior of said vessel and wherein said protective layer is formed so as to anchor onto said surface irregularities.

10. The apparatus of claim 9 wherein said surface irregularities comprise one or more ridges which also secures said window in place relative to said vessel.

11. The apparatus of claim 9 wherein said surface irregularities comprise a plurality of protuberances.

12. The apparatus of claim 1 wherein said ultraviolet radiation source produces a high intensity, directed light beam.

13. The apparatus of claim 12 wherein said ultraviolet radiation source comprises a laser.

* * * * *